United States Patent [19]

Krüger et al.

[11] Patent Number: 4,757,058

[45] Date of Patent: Jul. 12, 1988

[54] PHOSPHONIC ACID ESTER PESTICIDES

[75] Inventors: Bernd-Wieland Krüger, Wuppertal; Bernd Baasner, Leverkusen; Hermann Hagemann, Leverkusen; Bernhard Homeyer, Leverkusen; Benedikt Becker, Mettmann, all of Fed. Rep. of Germany

[73] Assignee: Bayer Aktiengesellschaft, Leverkusen, Fed. Rep. of Germany

[21] Appl. No.: 891,003

[22] Filed: Jul. 25, 1986

[30] Foreign Application Priority Data

Aug. 7, 1985 [DE] Fed. Rep. of Germany ....... 3528265

[51] Int. Cl.$^4$ .......................... A01N 57/02; C07F 9/40
[52] U.S. Cl. ...................................... 514/112; 558/167
[58] Field of Search .......................... 514/112; 558/167

[56] References Cited

U.S. PATENT DOCUMENTS 4,567,168 1/1986 Kruger et al. ...................... 558/167

FOREIGN PATENT DOCUMENTS 0044214 1/1982 European Pat. Off. ..
0058864 9/1982 European Pat. Off. ..
3528265 2/1987 Fed. Rep. of Germany .

Primary Examiner—Anton H. Sutto
Attorney, Agent, or Firm—Sprung Horn Kramer & Woods

[57] ABSTRACT

Pesticidally active novel α-cyano-(di)thiophosphonic acid esters of the formula

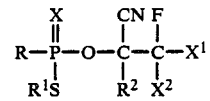

in which
X represents oxygen or sulphur,
R and $R^1$ are identical or different and represent alkyl,
$R^2$ represents hydrogen or optionally substituted alkyl and
$X^1$ and $X^2$ are identical or different and represent halogen, hydrogen or optionally substituted alkyl.

10 Claims, No Drawings

PHOSPHONIC ACID ESTER PESTICIDES

The invention relates to new O-(1-cyano-2-fluoroalkyl)-S-alkyl-(di)-thiophosphonic acid esters, a process for their preparation and their use as agents for combating pests, in particular as insecticides, acaricides and nematicides, and intermediate products for their preparation.

It has already been disclosed that certain O-(2,2,2-trihalogenoethyl)-S-(alkyl)-(di)thiophosphoric acid esters, such as, for example, O-(ethyl) O-(2,2,2-trifluoroethyl) S-(n-propyl) dithiophosphate (compare DE-OS (German Published Specification) No. 2,732,930), and O-(1-cyanoalkyl)-S-(alkyl)-O-(alkyl)-thiophosphoric(-phosphonic) acid esters (compare European Pat. Nos. A-44,214 and A-58,864) can be used for combating pests.

However, the insecticidal and acaricidal action of the known compounds is not always completely satisfactory, especially in the case of low concentrations of active compound and when low amounts are applied.

New α-cyano-(di)thiophosphonic acid esters of the general formula (I)

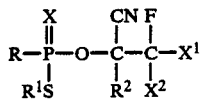

in which
X represents oxygen or sulphur,
R and $R^1$ are identical or different and represent alkyl,
$R^2$ represents hydrogen or optionally substituted alkyl and
$X^1$ and $X^2$ are identical or different and represent halogen, hydrogen or optionally substituted alkyl, have been found.

The new compounds of the general formula (I) are obtained by a process in which (di)thiophosphonic acid ester-halides of the general formula (II)

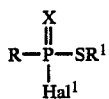

in which
R, $R^1$ and X have the abovementioned meaning and
$Hal^1$ represents halogen,
are reacted with β-fluoroalkanol derivatives of the general formula (III)

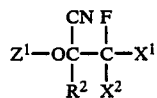

in which
$R^2$, $X^1$ and $X^2$ have the abovementioned meaning and
$Z^1$ represents hydrogen or one equivalent of an alkali metal or ammonium ion,
if appropriate in the presence of acid acceptors and if appropriate in the presence of diluents.

The new fluorinated α-cyano(di)thiophosphonic acid esters of the general formula (I) are distinguished by a high activity against animal pests, in particular by a high insecticidal and acaricidal activity. The active compounds according to the invention can furthermore be employed for combating nematodes. Moreover, some compounds also exhibit a fungicidal action, for example against *Pyricularia oryzae*.

Surprisingly, the fluorinated compounds of the general formula (I) show considerably more favorable insecticidal and acaricidal properties than corresponding known compounds.

In the general formulae, the alkyl radical R is straight-chain or branched and preferably contains 1 to 6, in particular 1 to 4 and especially preferably 1 or 2 carbon atoms. Examples which may be mentioned are methyl, ethyl, n- and i-propyl and n-, i-, s- and t-butyl.

The alkyl radical $R^1$ is straight-chain or branched and preferably contains 1 to 6, in particular 1 to 4 and especially preferably 3 or 4 carbon atoms, the branched propyl and butyl radicals being emphasized in particular. Examples which may be mentioned are methyl, ethyl, n- and i-propyl and n-, i-, s- and t-butyl.

The optionally substituted alkyl radicals $R^2$, $X^1$ and $X^2$ are straight-chain or branched and preferably certain 1 to 6, in particular 1 to 4 and especially preferably 1 or 2, carbon atoms. Examples which may be mentioned are methyl, ethyl, n- and i-propyl and n-, i-, s-and t-butyl. The alkyl radicals $R^2$, $X^1$ and $X^2$ are preferably unsubstituted.

Halogens $X^1$ and $X^2$ are fluorine, chlorine, bromine or iodine, preferably fluorine and chlorine, and in particular fluorine. $X^1$ and $X^2$ preferably simultaneously represent fluorine.

In the general formulae, the equivalents of an alkali metal ion $Z^1$ preferably represent a sodium, potassium or lithium ion, preferably a sodium or potassium ion.

$Hal^1$ denotes halogen, preferably chlorine, bromine or iodine, in particular chlorine or bromine and especially preferably chlorine.

In the general formulae, X preferably represents sulphur.

The optionally substituted alkyl radicals $R^2$, $X^1$ and $X^2$ can carry one or more, preferably 1 to 3 and in particular 1 or 2 identical or different substituents. Examples of substituents which may be mentioned are: alkoxy with preferably 1 to 4, in particular 1 or 2, carbon atoms, such as methoxy, ethoxy, n- and i-propyloxy and n-, i- and t-butyloxy; alkylthio with preferably 1 to 4, in particular 1 or 2, carbon atoms, such as methylthio, ethylthio, n- and i-propylthio and n- and t-butylthio; halogenoalkyl with preferably 1 to 4, in particular 1 or 2, carbon atoms and preferably 1 to 5, in particular 1 to 3, halogen atoms, it being possible for the halogen atoms to be identical or different and halogen atoms preferably being fluorine, chlorine or bromine, in particular fluorine, such as trifluoromethyl; hydroxyl; halogen, preferably fluorine, chlorine, bromine and iodine, in particular chlorine and bromine; cyano; and nitro.

The invention preferably relates to compounds of the general formula (I) in which
X represents oxygen or sulphur (preferably sulphur),
R and $R^1$ are identical or different and represent alkyl with 1 to 6 carbon atoms,
$R^2$ represents hydrogen or alkyl which has 1 to 6 carbon atoms and is optionally substituted by halogen (preferably chlorine) and
$X^1$ and $X^2$ are identical or different and represent halogen (preferably fluorine) or optionally substituted (preferably unsubstituted) alkyl with 1 to 6 carbon atoms.

The invention particularly relates to compounds of the general formula (I) in which X represents oxygen or sulphur (preferably sulphur), R and $R^1$ are identical or different and represent alkyl with 1 to 4 carbon atoms, $R^2$ represents hydrogen or methyl or ethyl which is optionally substituted by halogen (preferably chlorine) and $X^1$ and $X^2$ are identical or different and represent halogen (preferably fluorine), methyl or ethyl.

Particularly preferred compounds of the formula (I) are those in which

X represents oxygen or sulphur (preferably sulphur),

R represents methyl or ethyl, $R^1$ represents n- or i-propyl, or represents i-, s- or t-butyl, $R^2$ represents hydrogen, methyl or ethyl (preferably hydrogen or methyl) and $X^1$ and $X^2$ are identical or different and represent methyl or ethyl, or represent fluorine.

If ethane-S-(n-propyl)-dithio-phosphonic acid esterchloride and 1-cyano-2-fluoro-2-methylpropanol are used as starting substances, the reaction of these compounds can be outlined by the following equation:

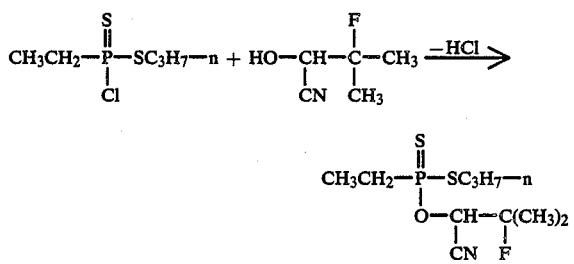

The compounds of the general formula (III) used as starting substances are known or can be prepared by known processes and methods (compare U.S. Pat. No. 2,662,915; J. Chem. Soc. 1951, 2329; and J. Chem. Soc. 1963, 3462).

Examples which may be mentioned of the compounds of the general formula (III) are:

$$Z^1-O-\underset{\underset{R^2}{|}}{\overset{\overset{CN}{|}}{C}}-\underset{\underset{X^2}{|}}{\overset{\overset{F}{|}}{C}}-X^1 \quad (III)$$

| $Z^1$ | $R^2$ | $X^1$ | $X^2$ |
|---|---|---|---|
| H | $CH_3$ | F | F |
| H | $C_2H_5$ | F | F |
| H | $C_3H_7$ | F | F |
| H | i-$C_3H_7$ | F | F |
| H | H | F | F |
| H | $CF_3$ | F | F |
| H | $CCl_3$ | Cl | Cl |
| H | $CFCl_2$ | Cl | Cl |
| H | $CF_2Cl$ | F | Cl |
| H | $CF_2Cl$ | Cl | Cl |
| H | $CH_2F$ | H | F |
| H | $CH_3$ | H | H |
| H | $CH_2Cl$ | H | H |
| H | $CF_2Cl$ | F | F |
| H | $CCl_3$ | F | F |
| H | H | F | Cl |
| H | H | $CH_3$ | $CH_3$ |
| H | H | $CH_3$ | $C_2H_5$ |
| H | H | $CH_3$ | $C_3H_7$ |
| H | H | $CH_3$ | i-$C_3H_7$, | and sodium, potassium, lithium or ammonium salts thereof.

The (di)thiophosphonic acid ester-halides of the general formula II to be used as starting substances are known and can be obtained by generally known processes and methods (compare European Pat. No. A-25,270 and German Pat. No. A-2,702,049).

Examples which may be mentioned are: S-methyl-, S-ethyl-, S-n-propyl-, S-i-propyl-, S-n-butyl-, S-i-butyl-, S-sec.-butyl- and S-(tert.-butyl)-methane(di)thiophosphonic acid chloride and bromide; S-methyl-, S-ethyl-, S-n-propyl-, S-i-propyl-, S-n-butyl-, S-i-butyl-, S-sec.-butyl- and S-(tert.-butyl)-ethane(di)thiophosphonic acid chloride and bromide; S-methyl-, S-ethyl-, S-n-propyl-, S-i-propyl-, S-n-butyl-, S-i-butyl-, S-sec.-butyl- and S-(tert.-butyl)-n-propane(di)thiophosphonic acid chloride and bromide; S-methyl-, S-ethyl, S-n-propyl-, S-i-propyl-, S-n-butyl-, S-i-butyl-, S-sec.-butyl- and S-(tert.-butyl)i-propane(di)thiophosphonic acid chloride and bromide; S-methyl-, S-ethyl-, S-n-propyl-, S-i-propyl-, S-n-butyl-, S-i-butyl-, S-sec.-butyl- and S-(tert.-butyl)-n-butane(di)thiophosphonic acid chloride and bromide; and S-methyl-, S-ethyl-, S-n-propyl-, S-i-propyl-, S-n-butyl-, S-i-butyl-, S-sec.-butyl- and S-(tert.-butyl)-i-butane(di)thiophosphonic acid chloride and bromide.

Possible diluents for the process according to the invention are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylene sulphone and hexamethylphosphoric acid triamide.

If appropriate, the process can be carried out in the presence of acid acceptors. All the customary acid-binding agents can be used as the acid acceptors. Acid-binding agents which have proved particularly suitable are alkali metal carbonates and alcoholates, such as sodium carbonate and potassium carbonate and sodium and potassium methylate and ethylate, and furthermore aliphatic, aromatic or heterocyclic amines, for example triethylamine, trimethylamine, dimethylaniline, dimethylbenzylamine and pyridine.

The process according to the invention is in general carried out at temperatures between −30° C. and 110° C. The range between 20° C. and 80° C. is preferred.

The reactions are in general carried out under normal pressure. Working up is effected by customary methods.

For carrying out the process according to the invention, 1 to 1.6 moles, preferably 1.1 to 1.4 moles, of β-fluorocyanohydrin derivative of the general formula (III) are employed per mole of the compound of the general formula (II).

The new compounds are in some cases obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. They are characterized by their refractive index.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculate.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta dometicus,* Gryllotalpa spp., *Locusta migratoria* migratorioides, *Melanoplus diffrentialis* and *Schistocerca gregaria.* From the order of the Dermaptera, for example, *Forficula auricularia.* From the order of the Isoptera, for example, Reticulitermes spp. From the order of the Anoplura, for example *Phylloxera vastatrix,* Pemphigus spp., *Pediculus humanus* corporis, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saisseti oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosom neustria, Euproctis chrysorrhoea,* Lymantria spp. *Bucculatrix thurberilla, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chils spp., *Pyraustas nubilalis, Ephestia kuehniela, Galleria mellonella Tineola bisselliella, Tinea pellionella, Hofmannophila pseudopretella, Cacoecia podana, Capua reticulana, Choristoneura fumiferana, Clysia ambiguella, Homona magnanima* and *Tortrix Viridana.* From the order of the Coleoptera, for example, *Anobium punctatum, Rhizopertha dominica Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amhimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypoderma spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scopio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Dilylenchus dipsaci, Tylenchulus semipenetrans,* Heterodera spp., Meloidogyne spp., Aphelenchoides spp., Longidorus spp., Xiphinema spp. and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide ankd dimethylsulphoxide, as well as water; by liquefied gaseous extenders or carriers are meant liquids which are gaseous at normal temperature and under normal pressure, for example aerosol propellane such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emusifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms, etc.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating parasites in the field of livestock husbandry and animal breeding, it being possible to achieve better results, for example higher milk yields, a heavier weight, a longer life and the like, by combating the pests.

The active compounds according to the invention are used in these fields in a known manner, such as by external use, for example in the form of dipping, spraying, pouring on and spotting on and dusting.

The activity of the compounds according to the invention may be illustrated with the aid of the following examples.

The following comparison compounds were employed:

$$\begin{array}{c} C_2H_5O \\ \diagdown \\ nC_3H_7S \end{array} \!\!\! \begin{array}{c} O \\ \| \\ P-O-CH-CH_3 \\ | \\ CN \end{array} \quad (A)$$

compare European Pat. No. A-44,214 (Example 4)

$$\begin{array}{c} C_2H_5 \\ \diagdown \\ nC_3H_7S \end{array} \!\!\! \begin{array}{c} S \\ \| \\ P-O-CH-CH \\ | \quad | \\ CN \quad CH_3 \end{array} \!\! \begin{array}{c} CH_3 \\ | \\ \end{array} \quad (B)$$

compare European Pat. No. A-58,864 (Example 67)

EXAMPLE A

Critical concentration test/soil insects

Test insect: *Phorbia antiqua* grubs (in the soil)
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of preparation Examples 1 and 3 showed a destruction of 100 and 95% respectively, at an active compound concentration of, for example, 2.5 ppm, while comparison compound (A) resulted in no destruction (0%) at the same concentration.

EXAMPLE B

Critical concentration test/soil insects

Test insect: *Diabrotica balteata* larvae in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into 0.5 liter pots and these are left to stand at 20° C.

Immediately after setting up the test, 6 pre-germinated grains of corn are placed in each pot. After 2 days, the corresponding test insects are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of preparation Examples 1 and 3 showed a degree of destruction of 100% at an active compound concentration of 1.25 ppm, while comparison compound (A) resulted in no destruction (0%) at the same concentration.

EXAMPLE D

Critical concentration test/nematodes

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds of preparation Examples 1 and 3 showed a degree of destruction of 95% at an active compound concentration of 5 ppm, while comparison compounds (A) and (B) resulted in a degree of destruction of 0% at the same concentration.

EXAMPLE D

Critical concentration test/nematodes

Test nematode: *Globodera rostochiensis* Solvent: 3 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, potatoes are sown in and the pots are kept at a greenhouse temperature of 18° C.

After six weeks, the potato roots are examined for cysts, and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds of preparation examples 1 and 3 showed a degree of destruction of 95% and 100% respectively at an active compound concentration of 20 ppm, while comparison compound (B) resulted in a degree of effectiveness of 0% at the same concentration.

EXAMPLE E

Drosophila test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

1 cm$^3$ of the preparation of the active compound is pipetted onto a filter paper disc (7 cm diameter). The wet disc is placed over the opening of a glass vessel containing 50 vinegar flies (*Drosophila melanogaster*) and is covered with a glass plate.

After the specified periods of time, the destruction in % is determined. 100% means that all the flies have been killed; 0% means that none of the flies have been killed.

In this test, for example, the compound of preparation example 3 showed a destruction of 100% after 1 day, at an active compound concentration of 0.001%, while the comparison compound (A) resulted in a destruction of 0% at the same concentration.

EXAMPLE F

Myzus test

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which have been heavily infested with peach aphids (*Myzus persicae*) are treated by being dipped into the preparation of active compound of the desired concentration.

After the specified periods of time, the destruction in % is determined. 100% means that all the aphids have been killed; 0% means that none of the aphids have been killed.

In this test, for example, the compound of preparation Example 3 showed a destruction of 95% after 1 day, at an active compound concentration of 0.01%, while comparison compound (B) resulted in no destruction at the same concentration.

EXAMPLE G

Doralis test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Vicia faba) which have been heavily infested with the black bean aphid (Doralis fabae) are each treated by being dipped into the preparation of the active compound of the desired concentration.

After the specified periods of time, the destruction in % is determined. 100% means that all the aphids have been killed; 0% means that none of the aphids have been killed.

In this test, for example, the compound of preparation Example 1 showed a destruction of 100% after 4 days, at an active compound concentration 0.1%, while comparison compound (B) resulted in a destruction of 0% at the same concentration.

The preparation of the compounds according to the invention may be illustrated with the aid of the following examples:

EXAMPLE 1

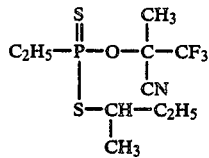

8.3 g (0.06 mole) of 1-cyano-1-methyl-2,2,2-trifluoroethanol and 8.3 g (0.06 mole) of potassium carbonate are taken in 100 ml of acetonitrile, and 10.8 g (0.05 mole) of ethanedithiophosphonic acid chloride S-sec.-butyl ester - dissolved in 20 ml of acetonitrile are added at an internal temperature of 5° to 10° C. The mixture is warmed at 60° C. for 1 day and evaporated in vacuo, the residue is taken up in $CH_2Cl_2$, the organic phase is washed with water and dried and volatile constituents are removed in vacuo. 14.2 g (89% of theory) of O-(1-cyano-1-trifluoromethyl)ethyl S-sec.-butyl ethanedithiophosphonate of refractive index $n_D^{20} = 1.4772$ remain as the residue.

The following compounds of the general formula (I) are obtained analogously to Example 1:

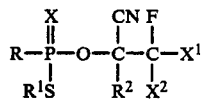

| Example No. | R | R¹ | X | R² | X¹ | X² | physical data ($n_D^{20}$) |
|---|---|---|---|---|---|---|---|
| 2 | C₂H₅ | sec.-C₄H₉ | S | H | CH₃ | CH₃ | |
| 3 | " | " | " | " | " | C₂H₅ | 1.5069 |
| 4 | " | " | " | " | " | CH₃ | |
| 5 | CH₃ | " | " | CH₃ | F | F | b.p.₀.₁ 65–76° C. |
| 6 | C₂H₅ | n-C₃H₇ | " | " | " | " | b.p.₀.₂ 80° C. |
| 7 | " | i-C₃H₇ | " | " | " | " | b.p.₀.₂ 80–90° C. |
| 8 | " | t-C₄H₉ | " | " | " | " | |
| 9 | " | sec.-C₄H₉ | O | " | " | " | |
| 10 | CH₃ | n-C₃H₇ | " | " | " | " | |
| 11 | C₂H₅ | i-C₄H₉ | S | " | " | " | b.p.₀.₂ 80° C. |
| 12 | CH₃ | sec.-C₄H₉ | O | " | " | " | |
| 13 | " | n-C₃H₇ | S | " | " | " | b.p.₀.₁ 66–74° C. |

It will be understood that the specification and examples are illustrative but not limitative of the present invention and that other embodiments within the spirit and scope of the invention will suggest themselves to those skilled in the art.

We claim:

1. An α-cyano-(di)thiophosphonic acid ester of the formula $$\begin{array}{c} X \\ \parallel \\ R-P-O-C-C-X^1 \\ | \quad\quad | \quad | \\ R^1S \quad R^2 \; X^2 \end{array} \begin{array}{c} CN \; F \\ | \; | \end{array}$$

in which
X represents oxygen or sulphur,
R represents alkyl with 1 to 4 carbon atoms,
R¹ represents alkyl with 1 to 6 carbon atoms,
R² represents alkyl which has 1 to 4 carbon atoms and
X¹ and X² represent fluorine.

2. A method of combating insects, acarids or nematodes which comprises applying to such insects, acarids or nematodes an insecticidally, acaricidally or nematocidally effective amount of a compound according to claim 1 and a diluent.

3. A compound according to claim 1, in which
X represents sulphur,
R represents methyl or ethyl,
R¹ represents n- or i-propyl, or represents i-, s- or t-butyl,
R² represents, methyl or ethyl and
X¹ and X² represent fluorine.

4. A compound according to claim 1, wherein such compound is O-(1-cyano-1-trifluoromethyl)ethyl S-sec.-butyl ethanedithiophosphonate of the formula

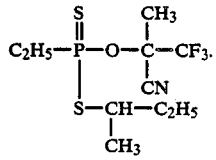

5. A compound according to claim 1, wherein such compound is O-(1-cyano-1-trifluoromethyl)ethyl S-sec.-butyl methanedithiophosphonate of the formula

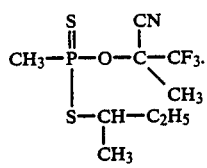

6. A compound according to claim 1, wherein such compound is O-(1-cyano-1-trifluoromethyl)ethyl S-n-propyl ethanedithiophosphonate of the formula

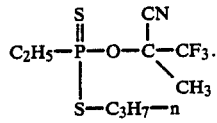

7. A compound according to claim 1, wherein such compound is O-(1-cyano-1-trifluoromethyl)ethyl S-i-propyl ethanethiophosphonate of the formula

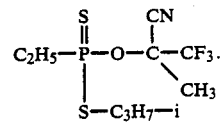

8. A compound according to claim 1, wherein such compound is O-(1-cyano-1-trifluoromethyl)ethyl S-n-propyl methanethiophosphonate of the formula

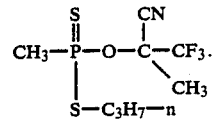

9. An insecticidal, acaricidal or nematocidal composition comprising an insecticidally, acaricidally or nematocidally effective amount of a compound according to claim 1 and a diluent.

10. The method according to claim 2, wherein such compound is
O-(1-cyano-1-trifluoromethyl)ethyl S-sec.-butyl ethanedithiophosphonate,
O-(1-cyano-1-trifluoromethyl)ethyl S-sec.-butyl methanedithiophosphonate,
O-1-cyano-1-trifluoromethyl)ethyl S-n-propyl ethanedithiophosphonate,
O-(1-cyano-1-trifluoromethyl)ethyl S-i-propyl ethanethiophosphonate or
O-(1-cyano-1-trifluoromethyl)ethyl S-n-propyl methanethiophosphonate.

* * * * *